United States Patent
Greer, Jr. et al.

(10) Patent No.: US 6,345,455 B1
(45) Date of Patent: *Feb. 12, 2002

(54) ORTHOTIC ARCH SUPPORT INCLUDING SELF-ADJUSTING ARCH CURVE AND METHOD OF USING ORTHOTIC

(75) Inventors: Jack K. Greer, Jr., Oak Ridge; W. Gilmer Reed, Jr., Strawberry Plains, both of TN (US)

(73) Assignee: Greer Reed Biomedical, LLC

( * ) Notice: Subject to any disclaimer, the term of this patent is extended or adjusted under 35 U.S.C. 154(b) by 0 days.

This patent is subject to a terminal disclaimer.

(21) Appl. No.: 09/578,653

(22) Filed: May 25, 2000

(51) Int. Cl.$^7$ .................................................. A61F 5/14
(52) U.S. Cl. ............................... 36/155; 36/91; 36/145; 36/161; 36/156
(58) Field of Search ............................ 36/91, 156, 145, 36/155–162, 166, 173, 88, 147, 174, 180, 182; 12/146 M, 142 N

(56) References Cited

U.S. PATENT DOCUMENTS

| | | | | |
|---|---|---|---|---|
| 717,523 A | * | 1/1903 | Arrowsmith | 36/166 |
| 815,897 A | * | 3/1906 | Arrowsmith | 36/173 |
| 899,367 A | * | 9/1908 | Winchell | 36/156 |
| 909,858 A | * | 1/1909 | Apgar | 36/161 |
| 1,289,738 A | * | 12/1918 | Gulick | 36/156 |
| 1,311,240 A | * | 7/1919 | Mayer | 36/157 |
| 2,022,247 A | * | 11/1935 | Lobel | 36/168 |
| 2,075,942 A | * | 4/1937 | Howell | 36/161 |
| 2,779,110 A | * | 1/1957 | Howell | 36/156 |
| 4,166,329 A | | 9/1979 | Herbig | |
| 4,813,157 A | | 3/1989 | Boisvert et al. | |
| 5,400,528 A | | 3/1995 | Skinner et al. | |
| 5,611,153 A | | 3/1997 | Fisher et al. | |
| 5,903,985 A | | 5/1999 | DeMarchi | |

* cited by examiner

Primary Examiner—Mickey Yu
Assistant Examiner—Jila M. Mohandesi
(74) Attorney, Agent, or Firm—Jack K. Greer, Jr.

(57) ABSTRACT

An orthotic arch support including an intrinsically self-adjusting medial longitudinal arch curve including a plurality of generally adjacent incisions being generally transverse across the medial longitudinal arch curve. The incisions originate at a medial side of the arch curve, thereby separating the curved arching surface into a plurality of resilient extensions. The plurality of extensions are compressed against each other and self-adjust the arch curve height and slopes during each step. As weight shifts onto the posterior slope, the height of the arch curve is decreased by limited compression of each extension against adjacent extensions during each stride. Each resilient extension flexibly rebounds to return the arch curve to an unweighted height when weight shifts off of the arch curve. A tensioning means is insertable underneath the extensions to adjust the height and slopes of the arch curve, providing for user adjustment of the arch curve height and slopes as foot pain is reduced during use. One orthosis, or a pair, are adjustable upon a physician's guidance and are movable by the user between shoes, requiring only one orthosis, or a pair, for therapeutic treatment of foot pain. A method of treatment of inflamation and pain in the foot includes utilizing an orthosis having an adjustable arch curve, and selectively and periodically adjusting the height and slope of the arch curve by manipulation of a tensioning means of the orthosis for therapeutic support and strengthening of the user's arches and feet.

19 Claims, 3 Drawing Sheets

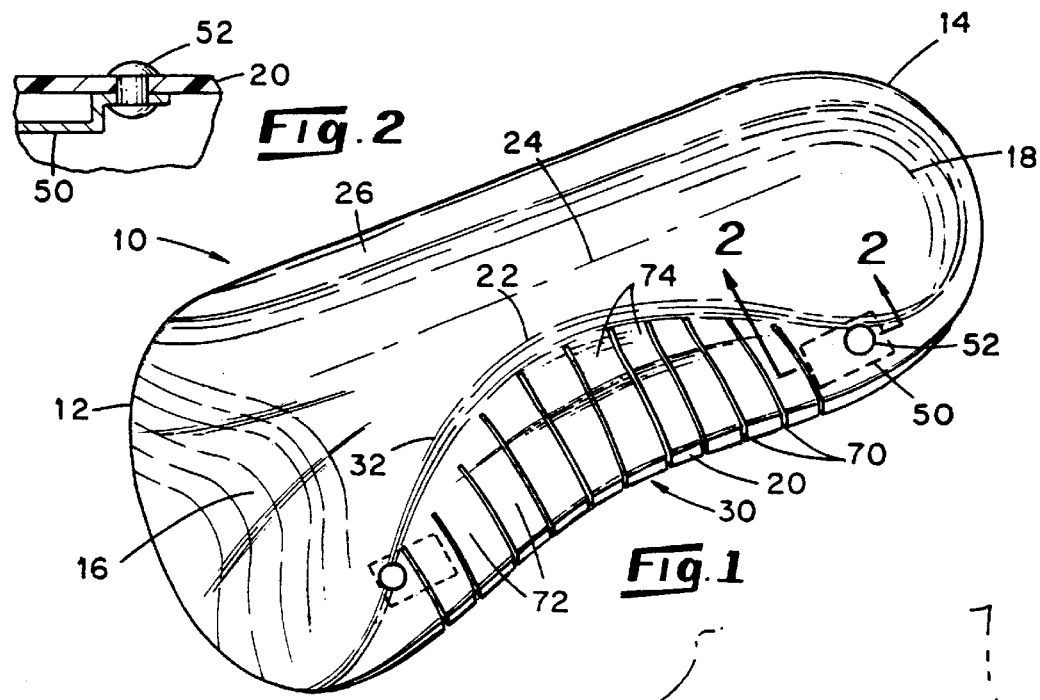
Fig. 2
Fig. 1
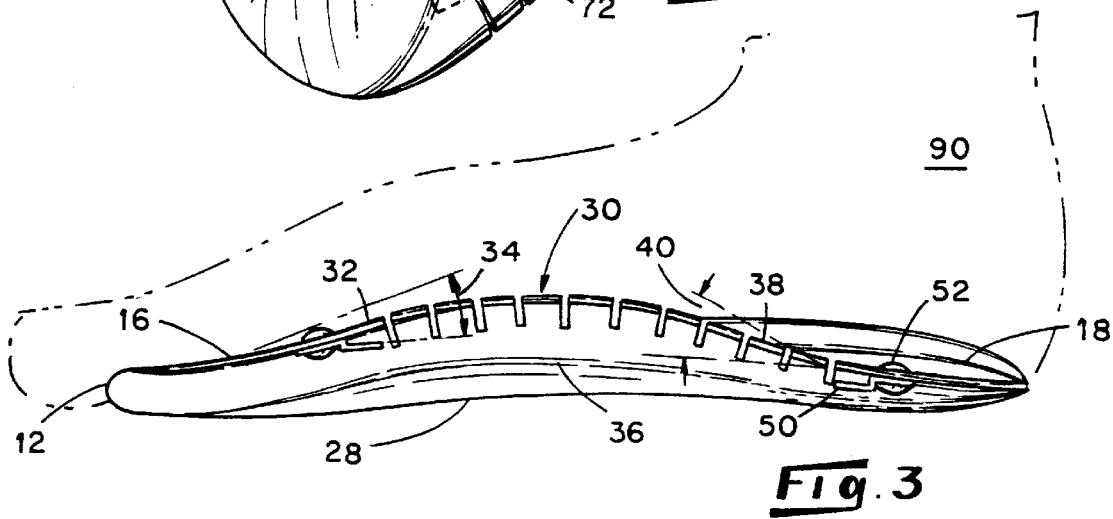
Fig. 3
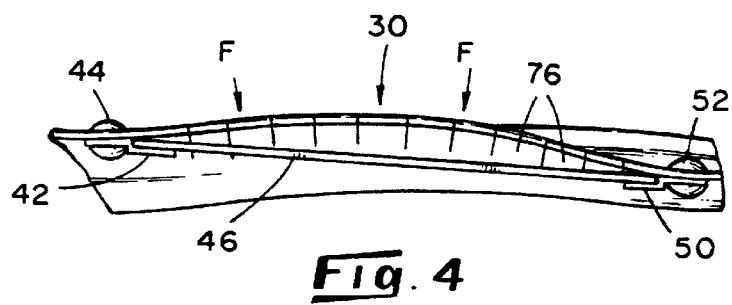
Fig. 4

ORTHOTIC ARCH SUPPORT INCLUDING SELF-ADJUSTING ARCH CURVE AND METHOD OF USING ORTHOTIC

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF INVENTION

1. Field of Invention

This invention relates generally to the field of therapeutic arch supports for feet, and more particularly to a therapeutic arch support having an arch curve being flexibly adjustable during use and a method of using the arch support.

2. Description of Related Art

Prior arch supports provide flexible cushioning material for support of an arch of a foot. Typical prior art insole supports have provided pliable cushion pads that can be utilized to build up the cushioning materials of a shoe insole for support of an arch. An adjustable arch support is described in U.S. Pat. No. 5,903,985, issued to DeMarchi, which discloses a sport boot that contains a sole overlaid by an upper boot having an internal support surface for the foot. Within the sport boot is a supporting structure that includes a flexible, elastically deformable series of upper tongues that extend upwards against the internal sidewall of the sport boot, and includes a deformable series of lower support blades that extend downwards toward the internal support surface of the sport boot. A central control blade is adjustable laterally with a control screw built into the base of the sport boot. The lateral movement of the central control blade adjusts the arch support provided in the horizontal direction to adapt the support blades against the arch of the user's foot. The control screw requires adjustment with a screw driver or similar tool while the sport boot sole is stationary to allow horizontal adjustment of the central control blade, thereby limiting the adjustment of the arch support to unweighted situations between strides by a wearer of the sport boot. The control blades are required to be installed as a unit into a specially designed sport boot having the required adjustment screws.

U.S. Pat. No. 5,611,153, issued to Fisher et al., discloses an insole for relieving bottom of heel pain by providing a pliable contoured insole with upwardly curved arch and a depression for the heel of the foot. The curved arch support is offered in a non-adjustable height.

U.S. Pat. No. 5,400,528, issued to Skinner et al., discloses a cushion insole including a separate arch support member which can be replaced as a unit with similar arch support members of various sizes to conform to the arch of the user. The arch support member can be moved forward or backwards and is required to be replaced as a unit with the cushion insole removed from the shoe of the user.

U.S. Pat. No. 4,813,157, issued to Boisvert, et al., discloses an adjustable shoe insole having superimposed layers of flexible pad materials such as leather and/or cork that are stacked for height adjustment of the arch support. The height of the arch area is adjusted by adding or removing of flexible pad materials when the insole is removed from the shoe and/or the foot is removed from the shoe and not contacting the insole.

U.S. Pat. No. 4,166,329, issued to Herbig, discloses an adjustable arch support having an interior arch member that is adjustable horizontally with an adjusting screw. The interior arch member is only moved as a unit and the curvature of the arch curve is not altered during horizontal movement. The arch support is inserted into a shoe as a unit and requires a hollow area to accommodate the adjusting screw which is turned by an adjusting tool while the shoe is stationary and unweighted.

The prior adjustable arch supports only provide arch adjustments that are generally lateral movements of members controlled by adjusting screws that require significant modifications to enclosing shoes or supporting sports boots. Therefore, there is a need for an improved adjustable arch orthotic providing therapeutic support of the longitudinal arch of a foot, with the medial longitudinal arch curve of the orthotic being intrinsically self-adjusting in height during each weighted and unweighted cycle during walking or running. There is another need for providing a method of treatment using an orthosis having an adjustable medial longitudinal arch curvature that is selectively adjustable in height and slope by the user of the orthosis under a physician's direction for treatment of heel spurs, plantar fasciitis, arch pain, tendinitis, and/or metatarsalgia. An additional need is to provide an orthotic having repetitively adjustable height and slope of the medial longitudinal arch curve, with the height and slope of the arch curve being extrinsically adjustable by user manipulation of a tensioning means connecting to the underside of the arch curve for therapeutic strengthening of the arch and foot to prevent recurrence of arch and foot pain.

Therefore, it is an object of the present invention to provide an adjustable arch curve orthotic for therapeutic support of the arch of the foot and that is removably insertable in any appropriately sized shoe and/or boot of a user.

It is another object of the present invention to provide an adjustable arch curve orthotic for therapeutic support of the arch of the foot and that is removably placable in and/or on an appropriately sized sandal of a user.

It is another object of the present invention to provide an arch curve orthosis having an inherently and repetitively adjustable arch curve height of the orthosis.

It is another object of the present invention to provide an adjustable orthosis providing rigid support for the forefoot and heel areas of the foot, and providing adjustable slopes of the anterior and posterior curves of the arch region of the orthosis.

It is another object of the present invention to provide a removably insertable orthotic having a medial longitudinal arch curvature that adjusts in height with each step taken by the user of the orthosis.

It is another object of the present invention to provide an orthosis having an adjustable medial longitudinal arch curvature that is selectively adjustable in height and slope by the user of the orthosis.

It is another object of the present invention to provide a method of utilizing an orthosis having an adjustable medial longitudinal arch curvature that supports the arch of the foot to prevent the arch from collapsing.

It is another object of the present invention to provide a method for treatment of inflamation and pain in the feet by applying an orthosis having an adjustable medial longitudinal arch curve that is selectively adjustable in height and slope by the user of the orthosis applied against the foot or feet of the user.

BRIEF SUMMARY OF INVENTION

Other subjects and advantages will be accomplished by the present invention which comprises an improved arch support orthosis including an arch curvature being self-adjustable during use, the arch support orthosis being fittable underneath the foot and being sized and shaped to be removably placed proximal a foot supporting surface of a shoe of a user. The arch support orthosis is sized for support of the foot from about the metatarsal bones of the foot to about the calcaneus bone of the foot, with the orthosis including a first or upper surface having a plurality of contours for support of the foot. The orthosis includes a second surface being downwardly faced for contact with the supporting surface of the shoe. The orthosis further includes a medial portion and a lateral portion on opposed sides of a medial longitudinal arch curve of the orthosis being sized to be removably placed underneath the medial longitudinal arch of the foot of a user.

The forefoot portion of the orthosis is shaped to be positionable underneath the metatarsal bones of the foot. The heel portion of the orthosis is shaped to be positionable underneath the calcaneus bone of the foot. The medial portion of the first or upper surface of the orthosis is shaped to be positionable underneath the arch of the foot, with the medial longitudinal arch curve being generally convex in curvature. The arch curve includes an anterior slope that is inclined at the leading portion of the arch curve and descends toward the forefoot portion of the orthosis. The arch curve includes a posterior slope that is inclined at the trailing portion of the arch curve and descends at an angle toward the heel portion to accommodate the angle of declination of the calcaneus heel bone. The arch curve includes a medial slope being oriented proximate the upper surface of the arch curve, with the medial slope inclined toward the longitudinal axis or midline of the orthosis. The arch curve further includes a plurality of extensions along the medial longitudinal arch curve, with the plurality of extensions being separated by a plurality of incisions along the upper surface of the medial longitudinal arch curve. The plurality of incisions originate along the interior side of the arch curve, and each of the plurality of incisions extend a distance along the arch curve toward the central midline of the orthotic and along the central arch slope of the orthosis. The plurality of incisions are generally transverse to the longitudinal axis or midline of the orthosis, and each incision terminates along the central arch slope of the orthosis.

During use, the plurality of extensions are forced together during each foot-strike by the force imposed by the foot of the user during normal transfer of force from the heel portion of the foot on the orthosis, and onto the arch curve of the orthosis, thereby collapsing the height of the arch curve until the width between the plurality of extensions is diminished and the plurality of extensions contact each other. Each of the plurality of extensions flexibly rebounds to the unweighted position by force being transferred off of the arch curve when the weight of the user is transferred onto the forefoot portion of the orthosis during a normal walking and/or running gait by the user wearing the orthosis. Therefore, the self-adjustable upper surface of the medial longitudinal arch curve flexibly supports a user's arch during unweighted use, and rigidly supports the user's arch at a certain height during each application of weight onto the medial longitudinal arch curve of the orthosis, providing therapeutic support of the user's arch depending on the application of force onto the orthosis by the user.

The plurality of incisions can be cuts through the upper surface of the arch curve with a distance between each extension of about 1 mm to about 2 mm in width. The arch curve can be additionally supported underneath with a removably positioned rigid support member being extended generally underneath the arch curve and parallel to the central axis or midline of the orthosis. The rigid support member can be selected from the group including a rigid bar, and/or a tensioned spring, and/or a two-piece cable having a central adjustable sleeve nut. The cable and adjustable sleeve nut can provide the ability for the user to adjust the tension and rigidity of the cable attached underneath the arch curve, thereby adjusting the anterior angle of the anterior slope, and the posterior angle of the posterior slope of the arch curve of the orthosis which provides for therapeutic treatment of foot conditions such as heel spurs, plantar fasciitis, arch pain, tendinitis associated with the tarsal bones, and/or metatarsalgia. The orthosis arch support having the self-adjustable arch curve can be formed to fit underneath either the right or left arch of the user's feet, and can be quickly removed and placed in any pair of shoes that the user wears, including dress shoes, casual shoes, athletic shoes, ski boots, and/or in sandals.

The present invention additionally discloses a method of treatment of inflamation and pain in the foot by application of an orthosis having an adjustable medial longitudinal arch curve, the method including selectively and periodically adjusting the height and slope of the arch curve by a user of the orthosis by manipulating a tensioning means associated with the orthosis for therapeutic support and strengthening of the user's arch to relieve inflamation associated with the plantar fascia and tendons of the foot.

BRIEF DESCRIPTION OF SEVERAL VIEWS OF THE DRAWINGS

The above mentioned features of the invention will become more clearly understood from the following detailed description of the invention contained herein, read together with the drawings in which:

FIG. 1 is a pictorial view of the arch support orthosis having a self-adjustable arch curvature of the present invention in an uncompressed configuration;

FIG. 2 is an enlarged partial sectioned view along lines 2—2 of FIG. 1 illustrating one embodiment of a mounting bracket of a tensioning means positioned underneath the self-adjustable arch curvature;

FIG. 3 is a side view illustrating the medial longitudinal arch curvature in an uncompressed configuration having a foot positioned on the orthosis;

FIG. 4 is a partial side view illustrating the medial longitudinal arch curvature in a compressed configuration including one embodiment of a tensioning means;

DETAILED DESCRIPTION OF THE INVENTION

Figure 5:
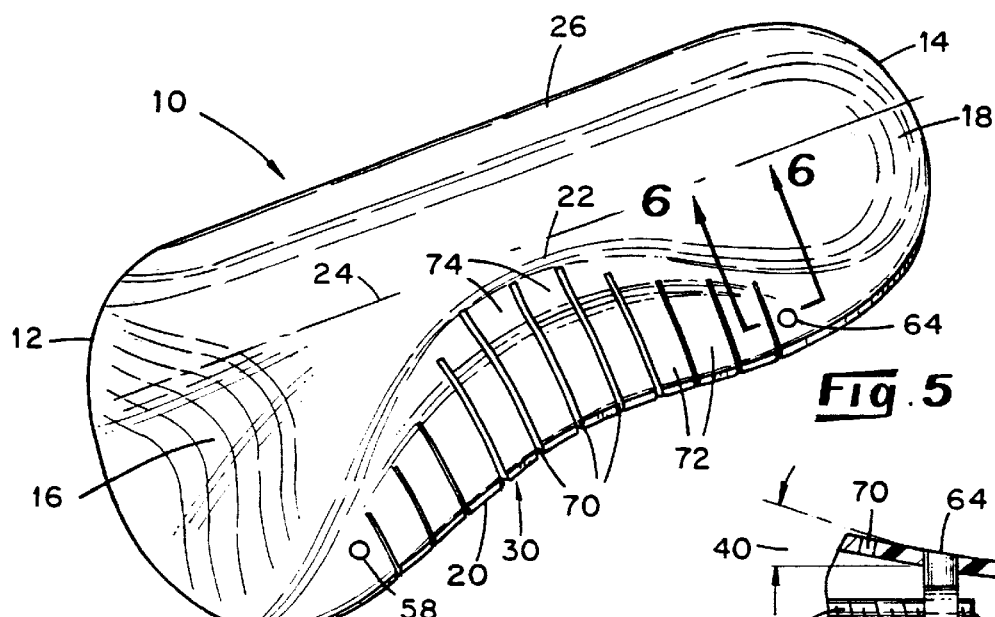
FIG. 5 is a pictorial view illustrating an alternative embodiment of the arch support orthosis having a self-adjustable arch curvature.
Figure 6:
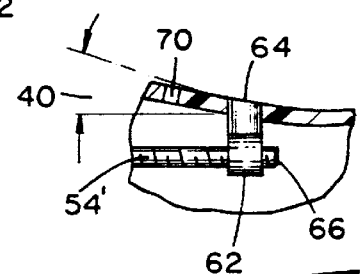
FIG. 6 is an enlarged partial sectioned view along lines 6—6 of FIG. 5 illustrating an alternative embodiment of a mounting bracket of a tensioning means positioned underneath the self-adjustable arch curvature.

An orthotic arch support system is disclosed incorporating various features of the present invention as illustrated generally for an arch support orthosis at 10 in FIGS. 1–9. The arch support orthosis is sized to support the foot of a user from approximately the forefoot, or anterior 12 region, to about the heel, or posterior 14 region of the foot 90 of a user (see FIGS. 1 and 3). The anterior 12 region includes a transverse arch curvature 16 for support of the metatarsal bones of the forefoot (see FIGS. 1 and 5). The posterior 14 region includes a concave heel section 18 for support of the calcaneus heel bone of the talus area of the foot 90 (see FIGS. 1 and 3).

The arch support orthosis 10 can be sized and shaped in various lengths, widths, and adjustable arch curve heights to accommodate users having a narrow, rigid foot with a high arch (pes cavus), a medium arch, or can be sized and shaped to accommodate users having a generally more flattened foot (pesplanus). The arch support orthosis 10 is removably placed upon a foot supporting surface such as the insole of any appropriately sized shoe or sandal, and underneath the foot of a user. The orthosis 10 can be shaped as for support of the arch of a right foot or the arch of a left foot, and can be utilized as a pair of right and left orthoses for simultaneous treatment of inflamation and pain in both user's feet. The orthosis 10 can be formed to fit large sized or smaller sized feet, and can be quickly removed and placed in any pair of shoes that the user wears, including dress shoes, casual shoes, athletic shoes, ski boots, and/or in sandals.

The arch support orthosis 10 includes an interior side 20 of the medial longitudinal arch curve 30 upper surface, and a central or medial arch slope 22 having a sloped portion extending toward the lengthwise axis or central midline 24. The medial arch curve slopes downwards in a forward direction towards the transverse arch curvature 16, and slopes downwards in a rearward direction towards the concave heel section 18. The medial arch curve of the orthosis 10 also slopes laterally outwards towards an outer edge 26 (see FIGS. 2 and 9). The lengthwise central midline 24 extends from the transverse arch curvature 16 to the concave heel section 18. On the outer side of the lengthwise central midline 24 is the outer edge 26 that is sloped slightly upwards along the outer perimeter of the orthosis 10 for support of the outer portion of the foot. The underside 28 of the orthosis 10 includes a curved portion 36 (see FIG. 3) that generally follows the medial longitudinal arch curve 30 of the upper surfaces of the orthosis 10.

Extending from the interior side 20 across to the central arch slope 22 is the upwards arching medial longitudinal arch curve 30 (see FIGS. 1 and 3), that includes a plurality of cuts or incisions 70 (see FIGS. 1 and 5, discussed below). The plurality of incisions 70 provide for inherent self-adjusting of the arch curve 30 in height, slope, and curvature during application of varying forces F (see FIG. 4) imposed onto the orthosis 10 from the user's foot 90 during standing, walking or running motions by the user.

The plurality of incisions 70 can be of about 0.5 millimeter to about 4.0 millimeter in width for each individual cut. One embodiment provides for each incision 70 to be about 1.0 millimeter to about 2.0 millimeter in width and originating along the interior side 20. Each incision 70 extends along the medial longitudinal arch curve 30 upper surface a certain length toward the central midline 24 (see FIGS. 1 and 5). Each incision is separated by a plurality of extensions 72 (see FIGS. 5 and 7), which are separated from each other when uncompressed by the forces F potentially placed onto the orthosis 10 by a foot 90 (see FIG. 3). When the user's foot compresses the arch curve 30, the plurality of extensions 72 are compressed against each other so that each side of each extension contacts 76 an adjacent side of an extension (see FIGS. 4 and 8), thereby creating a rigid arch curve 30 that can not be reduced in height or curvature unless the user applies excessive weight that exceeds the design capacity of the materials composing the orthosis 10. Each of the plurality of extensions 72 can be of varying widths and varying lengths. Extensions along the anterior slope 32 and the posterior slope 38 are shorter in length than the extensions that are oriented proximate the central arch slope 22 of the upper surface of the medial longitudinal arch curve 30. In one embodiment illustrated in FIG. 1, each of the four to five extensions 72 proximate the central arch slope 22 are approximately the same length and extend toward the central midline 24. In an alternative illustrated in FIG. 5, each of three to five extensions 72 proximate the central arch slope 22 are of different lengths and sized to extend along the varying curvature of central arch slope 22.

In one embodiment the plurality of incisions 70 are generally parallel as 25 illustrated in FIGS. 1 and 5. Each incision opens at the interior side 20 of medial arch curve. Each of the plurality of extensions 72 have an originating end or medial junction 74 that is proximate the descending slope of the respective anterior slope 32, the central arch slope 22, or the posterior slope 38. Each originating end or medial junction 74 serves as a cantilever having a rigidity and resiliency that is determined by the composition of the orthosis 10, which can be composed of a high density, generally rigid, polyester plastic. With the medial junctions 74 serving as a plurality of cantilevers, each extension 72 is returned to an unweighted configuration (see FIGS. 3 and 7) after the force is lessened against upper surface 30, thereby returning the medial longitudinal arch curve 30 to an unweighted curvature and height for support of the arch curve of a user's foot during sitting or reclining when the orthosis 10 is positioned against the user's foot.

Figure 7:
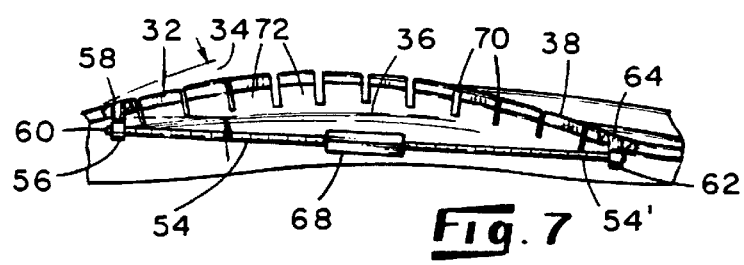
FIG. 7 is a partial side view of one embodiment of a tensioning means having an adjustable length with the medial longitudinal arch curvature in an uncompressed configuration.
Figure 8:
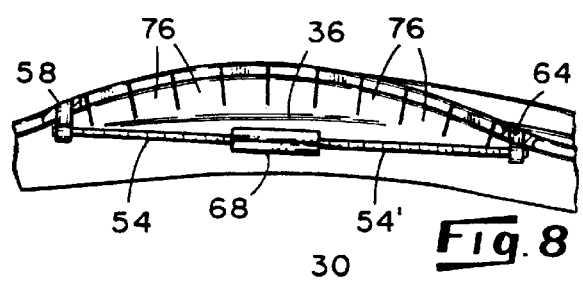
FIG. 8 is a partial side view of one embodiment of a tensioning means having a shortened length with the medial longitudinal arch curvature in a compressed configuration.
Figure 9:
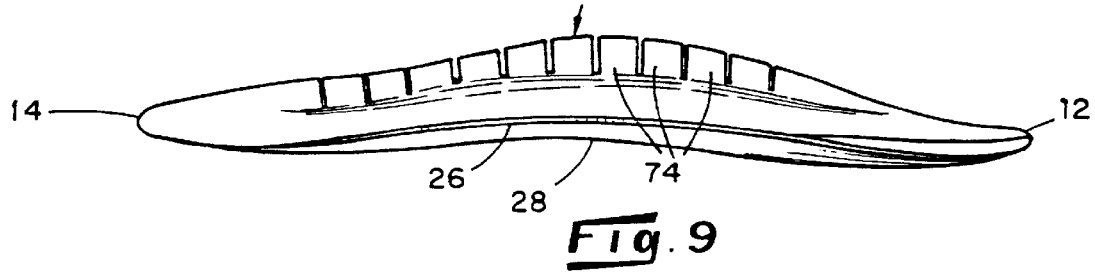
FIG. 9 is an opposing side view of FIG. 3 of the arch support orthosis having a self-adjustable arch curvature of the present invention.

The medial longitudinal arch curve 30 includes an anterior slope 32 of the forward surface of the orthosis having an anterior angle 34 (see FIG. 3) that can be adjusted in angle by insertion and manipulation of a tensioning means 46, 54 (see FIG. 4, 7 and 8). A posterior slope 38 includes a posterior angle 40 (see FIG. 3) that can be adjusted in angle by insertion and manipulation of the tensioning means 46, 54 (see FIGS. 4, 7 and 8). The tensioning means can include connection of removable bars 46 or tensioning means such as cables 54, 54' and an adjusting sleeve 68 positioned underneath the curved underside portion 36 of the medial longitudinal arch curve 30 of the orthosis 10.

An optimal therapeutic angle for the posterior angle 40 is about 15° for the descending posterior slope 38 of the medial longitudinal arch curve 30 upper surface to maintain therapeutic support of a user's foot. The angle 40 of the descending posterior slope 38, when adjusted to the optimal therapeutic angle by the user's manipulation of the tensioning means, provides support for the preferred orientation of the calcaneus heel bone in relation to the plantar fascia, which in medical terminology is referred to as the angle of declination, or alternately the angle that the plantar fascia forms when normally attached to the calcaneus heel bone. When the angle of declination decreases, as when the calcaneus bone rotates to a more horizontal orientation as occurs during aging and is termed "falling arches", there is resulting partial tearing of the plantar fascia attachment at the calcaneus heel bone. Therefore, posterior angle 40 of the descending posterior slope 38 is preferably maintained at about a 15° angle by the adjustable arch curve 30 of the orthosis 10 to support the calcaneus bone in the preferred position, thereby supporting the arch curve of the user's foot, while protecting the plantar fascia attachment from further tearing at the calcaneus bone, and minimizing reduction in the angle of declination.

A larger or smaller angle of slope for the anterior angle 34 of the leading anterior slope 32 can be incorporated into the arch curve 30 by manipulating the tensioning means 46, 54. By positioning the arch support orthosis 10 underneath the foot 90 of a user suffering with plantar fasciitis or associated tendinitis in the feet, the user's arch curve is optimally supported by the self-adjusting height of the medial longitudinal arch curve 30, and the optimal therapeutic angles of the posterior angle 40 and a similar angle for the anterior angle 34 can be maintained for support of each arch curve for either foot during each segment of every step taken by the user, and during sitting and relaxing, while wearing the arch support orthosis 10.

The height of the medial longitudinal arch curve 30, and the steepness of the anterior angle 34, and posterior angle 40, can be adjusted by a user with a minimal of effort and without a visit to the user's doctor by manipulating a tensioning means connectable to the curved underside portion 36 of the arch curve 30. As illustrated in FIGS. 1, 2, and 4, one embodiment of the tensioning means includes an anterior bracket 42 and a posterior bracket 50. The anterior bracket 42 is mounted with an opening end oriented toward the posterior of the orthosis 10, by connecting to the underside of the leading portion of the anterior slope 32 (see FIG. 4) by anterior mounting connector 44 such as a screwable post or a rivet that includes an upper surface that can protrude through the thickness of, and be generally flush with, the upper surface of the arch curve 30. The posterior bracket 50 is mounted with an opening end oriented toward the anterior of the orthosis 10, by connecting to the underside of the posterior portion of the posterior slope 38 (see FIGS. 1–4) by posterior mounting connector 52 such as a screwable post or a rivet that includes an upper surface that can protrude through the thickness of, and be generally flush with, the upper surface of the arch curve 30.

As a means for stiffening the flexibility of the arch curve 30, and/or increasing or decreasing the uncompressed height and the slope of the arch curve 30, at least one generally rigid bar 46 (see FIG. 4) can be removably positioned underneath the arch curve 30 between anterior bracket 42 and posterior bracket 50. The at least one bar 46 can be replaced with a wider, stiffer bar (not shown), if brackets 42, 50 are sized appropriately in width, or can be replaced with a thicker bar (not shown) to increase the rigidity of the arch curve 30. By including a removable bar 46, each user of a right-, or left-footed orthosis 10 can adjust the height and slope of each arch curve 30 to allow adjusting the height and slope of each arch curve 30 to provide an exacting fit of the shape of the user's left or right foot, and/or to increase or decrease the height and slope of the arch curve 30 as treatment progresses for the inflamation of the plantar fascia and tendons of the user's feet. A therapeutic method of treatment utilizing the orthosis 10 having the adjustable arch curve 30 is disclosed and discussed below, with the treatment method being supervised by an attending physician, or self-monitored by the user over a treatment period of two months to six months, or additional months for preventive treatment.

An alternative embodiment for the generally rigid bar 46 can include a curved or wedge shaped bar (not shown) that is insertable between brackets 42, 50, or a sequence of bars having progressively different rigidities and/or lengths that can be individually inserted each week and replaced sequentially to progressively raise the height of the user's arch curve, and progressively strengthen the user's arch curve of each foot, as needed for treatment of the user's inflamation and pain in the arch curve of his or her foot.

As illustrated in FIGS. 5–8, an alternative tensioning means positioned proximate the underside portion 36 of the orthosis 10 includes a first, generally rigid, length of cable 54 having an anterior end 60 connectable through an anterior eyelet 58. Eyelet 58 is connectable to the underside of the leading portion of the anterior slope 32 by anterior mounting connector 58 (see FIG. 7) such as a screwable post or a rivet that includes an upper surface that can protrude through the thickness of, and be generally flush with, the upper surface of the arch curve 30. A second, generally rigid and non-extensible, length of cable 54' having a posterior end 66 connectable through a posterior eyelet 62 is connectable to the underside of the posterior portion of the posterior slope 38 by posterior mounting connector 64 (see FIGS. 5–8) such as a screwable post or a rivet that includes an upper surface that can protrude through the thickness of, and be generally flush with, the upper surface of the arch curve 30. The lengths of cable 54, 54' can be composed of stranded wire, or stranded carbon-fiber materials that are generally non-extensible in the length dimension, and are generally rigid but can be minimally bent to allow flexing of the cables 54, 54' without breakage during high-force impacts on the orthosis 10 such as during running or participation of the user in sports requiring sudden stopping and pivoting of the feet. An alternative can utilize one cable (not shown) that is attachable at one end to anterior eyelet 58, or at the other cable end to posterior eyelet 62, with the opposed end of one cable being attachable to an adjustment means being attachable to the oppositely disposed eyelet from the eyelet attachable to the cable.

Each cable end 60, 66 and each end opposite of ends 60, 66 can be threaded, with each cable 54, 54' being connectable together at a mid-section underneath the underside portion 36 of the orthosis 10 by at least one rotatable sleeve nut 68 (see FIGS. 7 and 8). The sleeve nut 68 is generally known to those skilled in the art to be designed with a first, or anterior end, and a second, or posterior end, for grasping or attaching to a respective threaded end of one or two cables. The sleeve nut 68 can have an adjustment means attachable to the sleeve nut, or configured as part of the sleeve nut, that is rotatable to draw each respective threaded end of the cables together during tightening, or to extend apart during loosening for extension of each respective threaded end of the cables. By a user rotating sleeve nut 68 so as to draw cable ends 60, 66 together, the connectors 58, 64 are drawn closer together, thereby increasing the angle 34 of anterior slope 32 and the angle 40 of posterior slope 38, with resulting increase in the height of the arch curve 30 during uncompressed and compressed configurations of the arch curve 30. The height and slopes 32, 38 of the arch curve 30 can be reduced by the users manipulation of the 25 sleeve nut 68 to extend cable ends 60, 66 apart. Therefore, the height and slope of arch curve 30 of the orthosis 10 is self-adjustable during each foot-stride, and additionally the height and slope of the arch curve 30 is user-adjustable under a physician's direction to provide for a systematic method of therapeutic treatment of inflamation of the plantar fascia and associated tendons of the foot by variably supporting the user's arch curve with the arch curve 30, with resulting strengthening of the user's arch curve over a two month period to about a six month, or longer period as determined by the user and/or advising physician.

The inherently self-adjusting feature of the arch support orthosis 10 provides a therapeutic treatment for sufferer's of plantar fasciitis or associated tendinitis of the feet, by maintaining the preferred height of a low arch, medium arch, or high arch foot, thereby preventing the arch curve from collapsing excessively with each foot-step for prevention of excessive stretching of the plantar fascia and associated tendons of the foot during each step. As the arch curve of each foot flattens during the aging process and during sporting activities, the strong, rigid, and generally fully stretched plantar fascia of each foot can be stretched excessively during sports activities such as running, tennis, and/or vigorous walking, with resulting partial tearing of the plantar fascia attachment at the calcaneus heel bone. As tearing progresses, the condition identified as plantar fasciitis occurs, with continued pain due to irritation and inflamation of the plantar fascia during each step while a user participates in sports activities or general walking. Once partial tearing and inflamation occurs of the plantar fascia, re-injury can occur frequently, including as often as each morning as a sufferer takes his or her first step or two after a night of relaxation and partial healing of the plantar fascia of each foot.

To remedy the continued partial tearing and inflamation of the plantar fascia and/or associated tendons of the foot, a comfortable but generally rigid arch curve support of the sufferer's arch curve is required during each step, to minimize the stresses imposed on the plantar fascia attachment at the calcaneus heel bone. The arch support orthosis 10 provides comfort to a user by including a limited degree of height and slope adjustment during each step, while providing rigid arch support at a preselected height while weighted when the plurality of incisions 70 are compressed, thereby maintaining the minimum arch curve height for support of the user's arch as selected by the user and/or an advising physician. The additional therapeutic benefit of the arch support orthosis 10 is the tensioning means being attachable to the underside 28 of the orthosis 10. The tensioning means is adjustable in rigidity and/or tension by the user under the guidance of an advising physician, to provide an adjustable height and slope of the medial longitudinal arch curve 30 depending on what level of treatment of plantar fasciitis and associated tendinitis the user requires. During initial treatment, the arch curve 30 height and slopes can be increased to provide significant rigidity of the arch curve and additional support for each arch curve of the user's feet. During preventive and/or maintenance stages of treatment, the arch curve 30 height and slopes can be decreased somewhat by the user. Additionally, the user can utilize the same orthosis, or pair of orthoses, with arch curve 30 height and slope settings that are adjustable throughout the day depending on the walking and sitting activities of the user. Adjustments are easily made by the user the arch curve 30 height and slope by manipulating the tensioning means before and during sporting activities to provide additional support during repetitive impacts on the arch curve and feet of the user.

Figure 10:
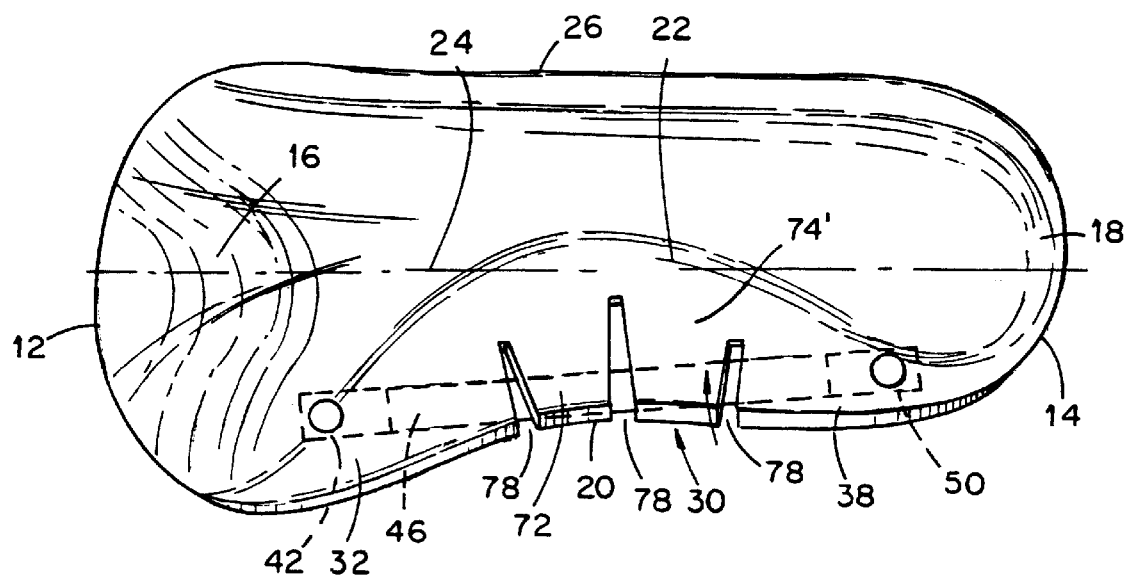
FIG. 10 is a pictorial view illustrating an alternative embodiment of the arch curve having angled incisions thereon.
Figure 11:
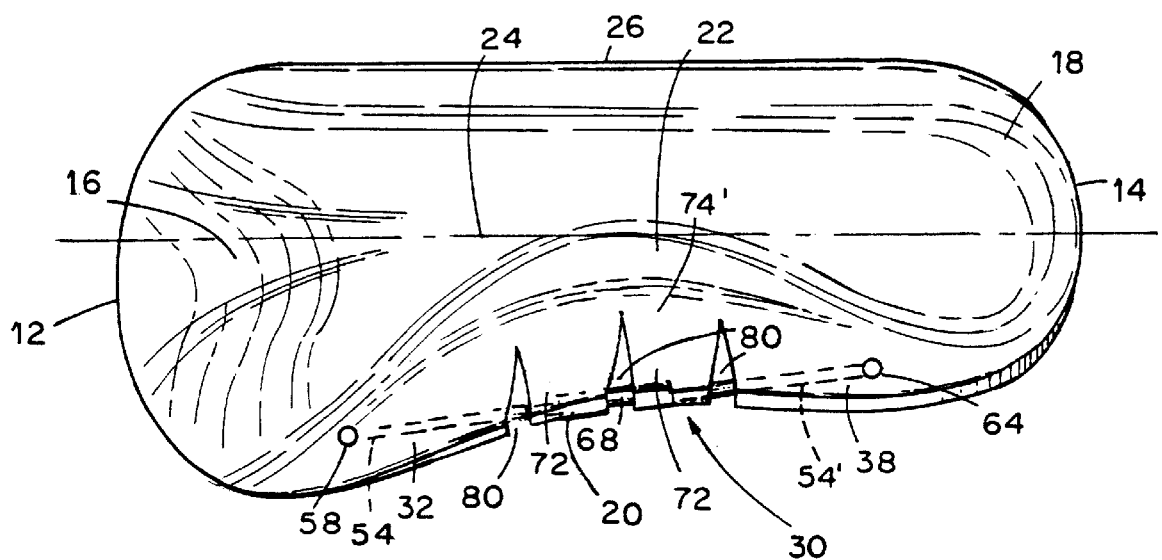
FIG. 11 is a pictorial view illustrating an alternative embodiment of the arch curve having v-shaped cuts thereon.

Alternative embodiments of the plurality of incisions 70 and associated plurality of extensions 72 can include angled incisions 78 (see FIG. 10) that originate at the interior side 20 of the arch curve 30, and are radially angled outwards toward the outer sloped edge 26, with the ends of the anterior angled incisions being oriented toward the anterior end 12, the ends of the posterior angled incisions being oriented toward the posterior end 14, and the ends of the middle, or upper surface incisions being oriented radially along the curvature of the central arch slope 22 and generally directed toward the central midline 24 of the orthosis. The plurality of uncut, bendable interior portions 74' (see FIG. 10) associated with the angled incisions 78, can each have a wider, more rigid base than the plurality of interior, medial junctions 74 between the generally straight incisions 70 (see FIGS. 1 and 5). In an additional alternative embodiment, the plurality of incisions can include one or more v-shaped cuts 80 (see FIG. 11), with the cut opening(s) originating at the interior side 20 of the arch curve 30. Each v-shaped cut includes a narrowed end of each cut that is oriented toward the central midline 24 of the orthosis, with the narrowed end closing of each v-shaped cut ending along the anterior slope 32, and/or along the central arch slope 22, and/or along the posterior slope 38 of the arch curve 30. Regardless of the shape of the incisions, whether straight incisions 70, angled incisions 78, or v-shaped incisions 80, the plurality of extensions 72 between each incision or cut are forced together during each foot-strike by force being transferred by the foot 90 of the user from the heel portion 18 and onto the arch curve 30 of the orthosis 10, thereby collapsing the height of the arch curve until the plurality of extensions 72 contact each other in a compressed position 76, with each of the plurality of extensions flexibly rebounding to the unweighted position by force being transferred by the foot of the user from the arch curve 30 and onto the forefoot portion 12 of the orthosis during each foot-strike by the user while wearing the orthosis 10.

Those skilled in the art will recognize that the additional alternative embodiment for the self-adjustable arch support orthosis includes a shortened self-adjustable arch support orthosis consisting of the medial longitudinal arch curve portion from the anterior angle of the anterior slope back to the posterior angle of the posterior slope. The alternative self-adjustable arch curve orthosis can include a fastening mechanism similar to velcro on the underside surface of the arch curve orthosis to allow the arch curve to be positioned underneath the arch of the foot, and to allow the arch curve to be removably placed in any pair of shoes that the user wears.

Alternative embodiments can also include a full length self-adjustable arch support orthosis extending from underneath the phalanges bones and the transverse arch of the foot, to the heel portion of the foot with the full length orthosis supporting the metatarsals, the underside of the foot and the plantar fascia of the longitudinal arch.

A further alternative embodiment can include a self-adjustable arch support orthosis placed in or onto the upper surface of a sandal, with a generally thin, resilient cover over the first surface of the orthosis and the upper surface of the adjustable arch curve. The self-adjustable arch support orthosis provides therapeutic support for the arch of a foot that is partially enclosed by a sandal, without the need for a complete upper shoe enclosure as required by prior insole devices.

From the foregoing description, it will be recognized by those skilled in the art that an improved arch support orthosis including intrinsic self-adjusting flexibility of the medial longitudinal arch curve of the orthosis is provided for therapeutic support of the arch of the foot in order to support the preferred height of a collapsing arch during walking and/or running motions, and to provide therapeutic support of the arch of the foot for treatment of heel spurs, plantar fasciitis, arch pain, tendinitis associated with the tarsal bones, and/or metatarsalgia.

The prior applications of arch supports were composed of flexible materials such as leather, or rigid materials such as plastic, that were not adjustable in arch curve height and arch curvature without insertion of additional pads of foam, flexible materials, or heating and bending rigid materials to increase the arch height and/or distance between the height of the arch curve and the concave heel portion of the shoe insert. In addition, prior applications of adjustable arch supporting members require a special boot or shoe enclosure that is not transferable from shoe to shoe, and is not adjustable in arch height and slope during each stride.

While a preferred embodiment is shown and described, it will be understood that it is not intended to limit the disclosure, but rather it is intended to cover all modifications and alternate devices and methods falling within the spirit and the scope of the invention as defined in the appended claims.

What is claimed is:

1. A foot support orthosis including an arch curvature being self-adjustable during use, the foot support orthosis being fittable underneath the foot and being sized and shaped to be removably placed proximal a foot supporting surface of a shoe, a sandal, and/or a boot covering the foot of a user, the foot support orthosis comprising:
   an orthosis being sized for support of the foot from underneath about the metatarsal bones of the foot, to underneath about the calcaneus bone of the foot, said orthosis having a first surface being contoured for support of the foot, having a second surface being downwardly faced for contact with the foot supporting surface of the shoe, and having a medial side and a lateral side on opposed sides of a central longitudinal axis of said orthosis;
   a forefoot portion of said first surface being arcuately shaped to be positionable underneath the metatarsal bones of the foot;
   a heel portion of said first surface being arcuately shaped to be positionable underneath the calcaneus bone of the foot; and
   a medial longitudinal arch curve proximate said medial side of said orthosis, said medial longitudinal arch curve being shaped to be positionable underneath the arch of the foot, said medial longitudinal arch curve having an upper surface being curved upwardly between said forefoot portion and said heel portion, said medial longitudinal arch curve including:
      an anterior slope being inclined from said upper surface of said medial longitudinal arch curve toward said forefoot portion of said orthosis;
      a posterior slope being inclined from said upper surface of said medial longitudinal arch curve toward said heel portion of said orthosis; and
      a medial slope being inclined from said upper surface of said medial longitudinal arch curve toward said lateral side of said orthosis; and
   a plurality of extensions along said medial longitudinal arch curve, said plurality of extensions having sides being separated by a plurality of incisions along said medial longitudinal arch curve, each of said plurality of extensions having interior ends being disposed in an arched curve along a length dimension of said medial side, said plurality of incisions including being originated along said medial side of said medial longitudinal arch curve, said plurality of incisions being extended a pre-selected distance along said medial longitudinal arch curve;
   whereby said sides of said plurality of extensions being forced together during each foot-strike by force being transferred by the foot of the user from said heel portion and onto said medial longitudinal arch curve of said orthosis, thereby collapsing the height of said medial longitudinal arch curve until said plurality of extensions contact each other, with each of said plurality of extensions flexibly rebounded to the unweighted position by force being transferred by the foot of the user from said medial longitudinal arch curve and onto said forefoot portion of said orthosis during each foot-strike by the user while wearing said orthosis.

2. The foot support orthosis of claim 1, wherein said plurality of incisions further comprises each of said plurality of incisions being generally transverse along said medial longitudinal arch curve of said orthosis, said plurality of incisions including:
   at least one anterior incision being ended proximate said anterior slope of said medial longitudinal arch curve;
   at least one posterior incision being ended proximate said posterior slope of said medial longitudinal arch curve; and
   at least one upper incision being extended along said upper surface of said medial longitudinal arch curve, said at least one upper incision being ended proximate said medial slope of said medial longitudinal arch curve.

3. The foot support orthosis of claim 1, wherein said plurality of extensions further comprises each extension being separated on each side of each extension by an incision being substantially parallel to each of said plurality of incisions, each incision being through said upper surface of said medial longitudinal arch curve, with each incision being between about 0.5 mm to about 4.0 mm in width.

4. The foot support orthosis of claim 3, wherein said medial longitudinal arch curve further comprises an underside surface having a curvature being generally parallel to said medial longitudinal arch curve curvature of said upper surface, said underside surface including:
   an anterior bracket attachable to said underside surface at about the anterior slope;
   a posterior bracket attachable to said underside surface at about the posterior slope;
   a rigid support member being extended generally parallel to said medial longitudinal length; and
   said support member being insertable between said anterior bracket and said posterior bracket, said support member being replaceable with like sized support members of differing flexibility and/or lengths, said support member being selected from the group consisting essentially of a generally straight bar, an arcuate bar, or a wedge shaped bar.

5. The foot support orthosis of claim 2, wherein said medial longitudinal arch curve further comprises an underside surface having a curvature being generally parallel to said medial longitudinal arch curve curvature of said upper surface, said underside surface having a tensioning means removably connectable between the underside of said anterior slope and said posterior slope of said medial longitudinal arch curve.

6. The foot support orthosis of claim 5, wherein said tensioning means comprises:
  at least one cable being generally rigid and having an anterior end and a posterior end;
  at least two connectors positioned at each end of said cable, including an anterior connector attached to said underside surface of said anterior slope, and a posterior connector attached to said underside surface of said posterior slope, said anterior end or said posterior end of said at least one cable being connectable to at least one of said at least two connectors; and
  an adjustment means having an anterior end and a posterior end, said adjustment means anterior end being connectable to said anterior connector, said adjustment means posterior end being connectable to said anterior end of said at least one cable, said posterior end of said at least one cable being connectable to said posterior connector, said adjustment means being rotatable to decrease or increase the length between said anterior connector and said posterior connector;
    whereby when the length between said anterior connector and said posterior connector is decreased by the user adjustment of said adjustment means, the height of said medial longitudinal arch curve is increased, and said anterior slope and said posterior slope is increased, and when the length between said anterior connector and said posterior connector is increased by the user adjustment of said adjustment means, the height of said medial longitudinal arch curve is decreased, and said anterior slope and said posterior slope is decreased of said medial longitudinal arch curve.

7. The foot support orthosis of claim 6, wherein said at least one cable further comprises an anterior cable and a posterior cable, said anterior cable having an anterior end being attached to said anterior connector and having an opposed cable end being threaded and attachable to said adjustment means, said posterior cable having a posterior end being attached to said posterior connector and having an opposed cable end being threaded and attachable to said adjustment means, said adjustment means including a sleeve nut being internally threaded and being rotatable in attachment with said respective threaded cable ends of said anterior cable and said posterior cable, wherein when the length between said anterior connector and said posterior connector is adjusted by the user adjustment of said sleeve nut and adjustment means thereby the height of said medial longitudinal arch curve, and said anterior slope and said posterior slope are adjustable to the height that the user prefers for support of the arch curve of the foot of the user by said medial longitudinal arch curve of the orthosis.

8. The foot support orthosis of claim 1, wherein said plurality of incisions further comprises a plurality of v-shaped incisions, said v-shaped incisions being originated along said medial side of said medial longitudinal arch curve, said plurality of v-shaped incisions including:
  at least one anterior incision being ended proximate said anterior slope of said medial longitudinal arch curve;
  at least one posterior incision being ended proximate said posterior slope of said medial longitudinal arch curve; and
  at least one upper incision being extended along said upper surface of said medial longitudinal arch curve, said at least one upper incision being ended proximate said medial slope of said medial longitudinal arch curve.

9. The foot support orthosis of claim 1, wherein said plurality of incisions further comprises a plurality of angled incisions extended radially from said medial side of said medial longitudinal arch curve, said radially angled incisions including:
  at least one anterior incision being ended proximate said anterior slope of said medial longitudinal arch curve;
  at least one posterior incision being ended proximate said posterior slope of said medial longitudinal arch curve; and
  at least one upper incision being extended along said upper surface of said medial longitudinal arch curve, said at least one upper incision being ended proximate said medial slope of said medial longitudinal arch curve.

10. A foot support orthosis including an arch curvature being self-adjustable during use, the foot support orthosis being fittable underneath the foot and being sized and shaped to be removably placed proximal a foot supporting surface of a shoe, a sandal, and/or a boot covering the foot of a user, the foot support orthosis comprising:
  an orthosis being sized for support of the foot from underneath about the metatarsal bones of the foot, to underneath about the calcaneus bone of the foot, said orthosis having a first surface being contoured for support of the foot, having a second surface being downwardly faced for contact with the foot supporting surface of the shoe, and having a medial side and a lateral side on opposed sides of a central longitudinal axis of said orthosis;
  a forefoot portion of said first surface of said orthosis being arcuately shaped to be positionable underneath the metatarsal bones of the foot;
  a heel portion of said first surface of said orthosis being arcuately shaped to be positionable underneath the calcaneus bone of the foot;
  a medial longitudinal arch curve proximate said medial side of said orthosis, said medial longitudinal arch curve being shaped to be positionable underneath the arch of the foot, said medial longitudinal arch curve having an upper surface being curved upwardly between said forefoot portion and said heel portion, said medial longitudinal arch curve including:
    an anterior slope being inclined from said upper surface of said medial longitudinal arch curve toward said forefoot portion of said orthosis;
    a posterior slope being inclined from said upper surface of said medial longitudinal arch curve toward said heel portion of said orthosis; and
    a medial slope being inclined from said upper surface of said medial longitudinal arch curve toward said lateral side of said orthosis; and
  a plurality of extensions along said medial longitudinal arch curve, said plurality of extensions being separated by a plurality of incisions along said medial longitudinal arch curve, each of said plurality of extensions having interior ends being disposed along an arched curve proximate a substantially aligned length dimension of said medial side, said plurality of incisions including being originated along said medial side of said medial longitudinal arch curve of said orthosis, said plurality of incisions being extended a pre-selected distance along said medial longitudinal arch curve;
    whereby said plurality of extensions being forced together during each foot-strike by force being transferred by the foot of the user from said heel portion and onto said medial longitudinal arch curve of said orthosis, thereby collapsing the height of said medial longitudinal arch curve until said plurality of extensions contact each other, with each of said plurality of extensions flexibly rebounded to the unweighted position by force being transferred by the foot of the user from said medial longitudinal arch curve and onto said forefoot portion of said orthosis during each foot-strike by the user while wearing said orthosis.

11. The foot support orthosis of claim 10, wherein said plurality of incisions further comprise each of said plurality of incisions being generally along said upper surface of said medial longitudinal arch curve, each of said plurality of incisions including:
  at least one anterior incision being ended proximate said anterior slope of said medial longitudinal arch curve;
  at least one posterior incision being ended proximate said posterior slope of said medial longitudinal arch curve; and
  at least one upper incision being extended along said upper surface of said medial longitudinal arch curve, said at least one upper incision being ended proximate said medial slope of said medial longitudinal arch curve.

12. The foot support orthosis of claim 11, wherein said medial longitudinal arch curve including an underside surface having a curvature being generally parallel to said medial longitudinal arch curve curvature of said upper surface, said underside surface including:
  an anterior bracket attachable to said underside surface at about the anterior slope;
  a posterior bracket attachable to said underside surface at about the posterior slope;
  a rigid support member being extended generally parallel to said medial longitudinal length; and
  said support member being an insertable between said anterior bracket and said posterior bracket, said support member being replaceable with like sized support members of differing flexibility and/or lengths, said support member being selected from the group consisting essentially of a generally straight bar, an arcuate bar, or a wedge shaped bar.

13. The foot support orthosis of claim 11, wherein said medial longitudinal arch curve further comprises an underside surface having a curvature being generally parallel to said medial longitudinal arch curve of said upper surface, said underside surface having a tensioning means removably connectable between said underside surface of said anterior slope and said underside surface of said posterior slope of said medial longitudinal arch curve, said tensioning means including:
  at least one cable being generally rigid and having an anterior end and a posterior end extended respectively between said underside surface of said anterior slope and said underside surface of said posterior slope;
  at least two connectors positioned and connectable to each end of said cable, said connectors including an anterior connector being attached to said underside surface of said anterior slope, and a posterior connector being attached to said underside surface of said posterior slope; and
  an adjustment means being connectable between said anterior end of said cable and said anterior connector, or said adjustment means being connectable between said posterior end of said cable end and said posterior connector, said adjustment means being adjustable to decrease the length between, or to increase the length between said anterior connector and said posterior connector;
  whereby when the length between said anterior connector and said posterior connector is adjusted by the user adjustment of said adjustment means thereby the height of said medial longitudinal arch curve, and said anterior slope and said posterior slope are adjustable to the height that the user prefers for support of the arch curve of the foot of the user by said medial longitudinal arch curve of the orthosis.

14. The foot support orthosis of claim 13, wherein said at least one cable further comprises an anterior cable and a posterior cable, said anterior cable having an anterior end being attached to said anterior connector and having an opposed cable end being threaded and attachable to said adjustment means, said posterior cable having a posterior end being attached to said posterior connector and having an opposed cable end being threaded and attachable to said adjustment means being internally threaded, said adjustment means being adjustable in attachment with said respective threaded cable ends of said anterior cable and said posterior cable, wherein when the length between said anterior connector and said posterior connector is adjusted by the user adjustment of said adjustment means thereby the height of said medial longitudinal arch curve, and said anterior slope and said posterior slope are adjustable to the height that the user prefers for support of the arch curve of the foot of the user by said medial longitudinal arch curve of the orthosis.

15. A foot support orthosis including an arch curvature being self-adjustable during use, the foot support orthosis being fittable underneath the foot and being sized and shaped to be removably placed proximal a foot supporting surface of a shoe, a sandal, and/or a boot covering the foot of a user, the foot support orthosis comprising:
  an orthosis being sized for support of the foot from underneath about the metatarsal bones of the foot, to underneath about the calcaneus bone of the foot, said orthosis having a first surface being contoured for support of the foot, having a second surface being downwardly faced for contact with the foot supporting surface of the shoe, and having a medial side and a lateral side on opposed sides of a central longitudinal axis of said orthosis;
  a forefoot portion of said first surface being arcuately shaped to be positionable underneath the metatarsal bones of the foot;
  a heel portion of said first surface being arcuately shaped to be positionable underneath the calcaneus bone of the foot; and
  a medial longitudinal arch curve proximate said medial side of said orthosis, said medial longitudinal arch curve being shaped to be positionable underneath the arch of the foot, said medial longitudinal arch curve having an upper surface being curved upwardly between said forefoot portion and said heel portion, said medial longitudinal arch curve including:
    an anterior slope being inclined from said upper surface of said medial longitudinal arch curve toward said forefoot portion of said orthosis;
    a posterior slope being inclined from said upper surface of said medial longitudinal arch curve toward said heel portion of said orthosis; and
    a medial slope being inclined from said upper surface of said medial longitudinal arch curve toward said lateral side of said orthosis; and a plurality of extensions along said medial longitudinal arch curve, said plurality of extensions having sides being separated by a plurality of incisions along said medial longitudinal arch curve, each of said plurality of extensions having interior ends being disposed in an arched curve along a length dimension of said medial side, said plurality of incisions including being originated along said medial side of said medial longitudinal arch curve orthosis, said plurality of incisions further including:
- at least one anterior incision being ended proximate said anterior slope of said medial longitudinal arch curve;
- at least one posterior incision being ended proximate said posterior slope of said medial longitudinal arch curve; and
- at least one upper incision being extended along said upper surface of said medial longitudinal arch curve, said at least one upper incision being ended proximate said medial slope of said medial longitudinal arch curve;

whereby said sides of said plurality of extensions being forced together during each foot-strike by force being transferred by the foot of the user from said heel portion and onto said medial longitudinal arch curve of said orthosis, thereby collapsing the height of said medial longitudinal arch curve until said plurality of extensions sides contact each other, thereby forming a compressed rigid position of said medial longitudinal arch curve, with each of said plurality of extensions flexibly rebounded to an unweighted position by force being transferred by the foot of the user from said medial longitudinal arch curve and onto said forefoot portion of said orthosis during each foot-strike by the user while wearing said orthosis; and said medial longitudinal arch curve further comprises an underside surface having a curvature being generally parallel to said medial longitudinal arch curve curvature of said upper surface, said underside surface having a tensioning means removably connectable between the underside of said anterior slope and said posterior slope of said medial longitudinal arch curve;

wherein said tensioning means comprises:
- an anterior cable and a posterior cable, each cable being generally rigid in a length dimension, and having an anterior end and a posterior end;
- at least two connectors positioned a length apart along said underside surface of said medial longitudinal arch curve, including an anterior connector attached to said underside surface of said anterior slope, and a posterior connector attached to said underside surface of said posterior slope, said anterior cable and said posterior cable being connectable between said at least two connectors; and
- an adjustment means having an anterior end and a posterior end, said adjustment means anterior end being connectable between said anterior cable and said posterior cable, said adjustment means being rotatable to decrease or increase the length between said anterior connector and said posterior connector; whereby when the length between said anterior connector and said posterior connector is decreased by the user adjustment of said adjustment means, the height of said medial longitudinal arch curve is increased, and said anterior slope and said posterior slope is increased, and when the length between said anterior connector and said posterior connector is increased by the user adjustment of said adjustment means, the height of said medial longitudinal arch curve is decreased, and said anterior slope and said posterior slope is decreased of said medial longitudinal arch curve.

16. The foot support orthosis of claim 15, wherein said plurality of incisions further comprises a plurality of v-shaped incisions, said v-shaped incisions being originated along said medial side of said medial longitudinal arch curve, said plurality of v-shaped incisions including:
- at least one anterior incision being ended proximate said anterior slope of said medial longitudinal arch curve;
- at least one posterior incision being ended proximate said posterior slope of said medial longitudinal arch curve; and
- at least one upper incision being extended along said upper surface of said medial longitudinal arch curve, said at least one upper incision being ended proximate said medial slope of said medial longitudinal arch curve.

17. A foot support orthosis including an arch curvature being self-adjustable during use, the foot support orthosis being fittable underneath the foot and being sized and shaped to be removably placed proximal a foot supporting surface of a shoe, a sandal, and/or a boot covering the foot of a user, the foot support orthosis comprising:
- an orthosis being sized for support of the foot from underneath about the metatarsal bones of the foot, to underneath about the calcaneus bone of the foot, said orthosis having a first surface being contoured for support of the foot, having a second surface being downwardly faced for contact with the foot supporting surface of the shoe, and having a medial side and a lateral side on opposed sides of a central longitudinal axis of said orthosis;
- a forefoot portion of said first surface of said orthosis being arcuately shaped to be positionable underneath the metatarsal bones of the foot;
- a heel portion of said first surface of said orthosis being arcuately shaped to be positionable underneath the calcaneus bone of the foot; and
- a medial longitudinal arch curve proximate said medial side of said orthosis, said medial longitudinal arch curve being shaped to be positionable underneath the arch of the foot, said medial longitudinal arch curve having an upper surface being curved upwardly between said forefoot portion and said heel portion, said medial longitudinal arch curve including a plurality of extensions thereon, said plurality of extensions being separated by a plurality of incisions therein said medial longitudinal curve, further including:
  - an anterior slope being inclined from said upper surface of said medial longitudinal arch curve toward said forefoot portion of said orthosis, said anterior slope having an anterior incision therein, said anterior incision being ended on said anterior slope;
  - a posterior slope being inclined from said upper surface of said medial longitudinal arch curve toward said heel portion of said orthosis, said posterior slope having a posterior incision therein, said posterior incision being ended on said posterior slope; and
  - a medial slope being inclined from said upper surface of said medial longitudinal arch curve toward said lateral side of said orthosis, said medial slope having a medial incision therein, said posterior incision being ended on said medial slope; and each of said plurality of extensions having interior ends being disposed along an arched curve proximate a substantially aligned length dimension of said medial side;

whereby said plurality of extensions being forced together during each foot-strike by force being transferred by the foot of the user from said heel portion and onto said medial longitudinal arch curve of said orthosis, thereby collapsing the height of said medial longitudinal arch curve until said plurality of extensions contact each other, thereby forming a compressed position of said medial longitudinal arch curve, with each of said plurality of extensions flexibly rebounded to an unweighted position of said medial longitudinal arch curve by force being transferred by the foot of the user from said medial longitudinal arch curve and onto said forefoot portion of said orthosis during each foot-strike by the user while wearing said orthosis.

18. The foot support orthosis of claim 17, wherein said medial longitudinal arch curve further comprises an underside surface having a curvature being generally parallel to said medial longitudinal arch curve of said upper surface, said underside surface having a tensioning means removably connectable between said underside surface of said anterior slope and said underside surface of said posterior slope of said medial longitudinal arch curve, said tensioning means including:

at least one cable being generally rigid and having an anterior end and a posterior end extended respectively between said underside surface of said anterior slope and said underside surface of said posterior slope;

at least two connectors positioned and connectable to each end of said cable, said connectors including an anterior connector being attached to said underside surface of said anterior slope, and a posterior connector being attached to said underside surface of said posterior slope; and an adjustment means being connectable between said anterior end of said cable and said anterior connector, or said adjustment means being connectable between said posterior end of said cable end and said posterior connector, said adjustment means being adjustable to decrease the length between, or to increase the length between, said anterior connector and said posterior connector;

whereby when the length between said anterior connector and said posterior connector is adjusted by the user adjustment of said adjustment means thereby the height of said medial longitudinal arch curve, and said anterior slope and said posterior slope are adjustable to the height that the user prefers for support of the arch curve of the foot of the user by said medial longitudinal arch curve of the orthosis.

19. The foot support orthosis of claim 18, wherein said plurality of incisions further comprises a plurality of angled incisions extended radially from said medial side of said medial longitudinal arch curve, said radially angled incisions including:

at least one anterior incision being ended proximate said anterior slope of said medial longitudinal arch curve;

at least one posterior incision being ended proximate said posterior slope of said medial longitudinal arch curve; and at least one upper incision being extended along said upper surface of said medial longitudinal arch curve, said at least one upper incision being ended proximate said medial slope of said medial longitudinal arch curve.

\* \* \* \* \*